United States Patent
Thomas et al.

(10) Patent No.: US 6,872,366 B2
(45) Date of Patent: Mar. 29, 2005

(54) METHOD AND APPARATUS FOR USING OZONE AS DISINFECTANT

(75) Inventors: Robert Malcolm Thomas, Alvin, TX (US); Karl Frederick Thomas, Alvin, TX (US)

(73) Assignee: Marhoc, Inc., Alvin, TX (US)

( * ) Notice: Subject to any disclaimer, the term of this patent is extended or adjusted under 35 U.S.C. 154(b) by 0 days.

(21) Appl. No.: 09/932,557

(22) Filed: Aug. 17, 2001

(65) Prior Publication Data
US 2003/0035764 A1 Feb. 20, 2003

(51) Int. Cl.$^7$ ................................................. B01J 19/08
(52) U.S. Cl. .......................... 422/186.07; 422/186.15
(58) Field of Search ....................... 422/186.07, 186.15, 422/186.14

(56) References Cited

U.S. PATENT DOCUMENTS

| | | | |
|---|---|---|---|
| 1,096,991 A | * | 5/1914 | Blanchard .................... 422/186 |
| 3,549,528 A | | 12/1970 | Armstrong |
| 4,156,653 A | * | 5/1979 | McKnight ............... 422/186.09 |
| 4,375,812 A | | 3/1983 | Vaseen et al. |
| 5,241,803 A | | 9/1993 | Griffin |
| 5,266,275 A | * | 11/1993 | Faddis ......................... 422/116 |
| 5,344,622 A | | 9/1994 | Faddis et al. |
| 5,501,844 A | | 3/1996 | Kasting, Jr. et al. |
| 5,914,089 A | | 6/1999 | Murakami et al. |
| 6,120,739 A | | 9/2000 | Thomas et al. |

* cited by examiner

Primary Examiner—Kishor Mayekar
(74) Attorney, Agent, or Firm—Nick A. Nichols, Jr.

(57) ABSTRACT

An apparatus for generating an effective concentration of ozone for killing bacteria, viruses and other harmful microorganisms includes a housing having an ozone chamber defining an enclosed space for containing elevated concentrations of ozone. The ozone chamber includes ports providing access to the interior of the ozone chamber. A second chamber of the apparatus houses an ozone reactor. A programmable control circuit operates both the ozone reactor and a pump for directing ambient air to the ozone reactor. The control circuit includes a motion detector mounted in the ozone chamber for activating the ozone generator of the invention and initiating the generation of ozone directed into the ozone chamber of the apparatus of the invention.

13 Claims, 2 Drawing Sheets

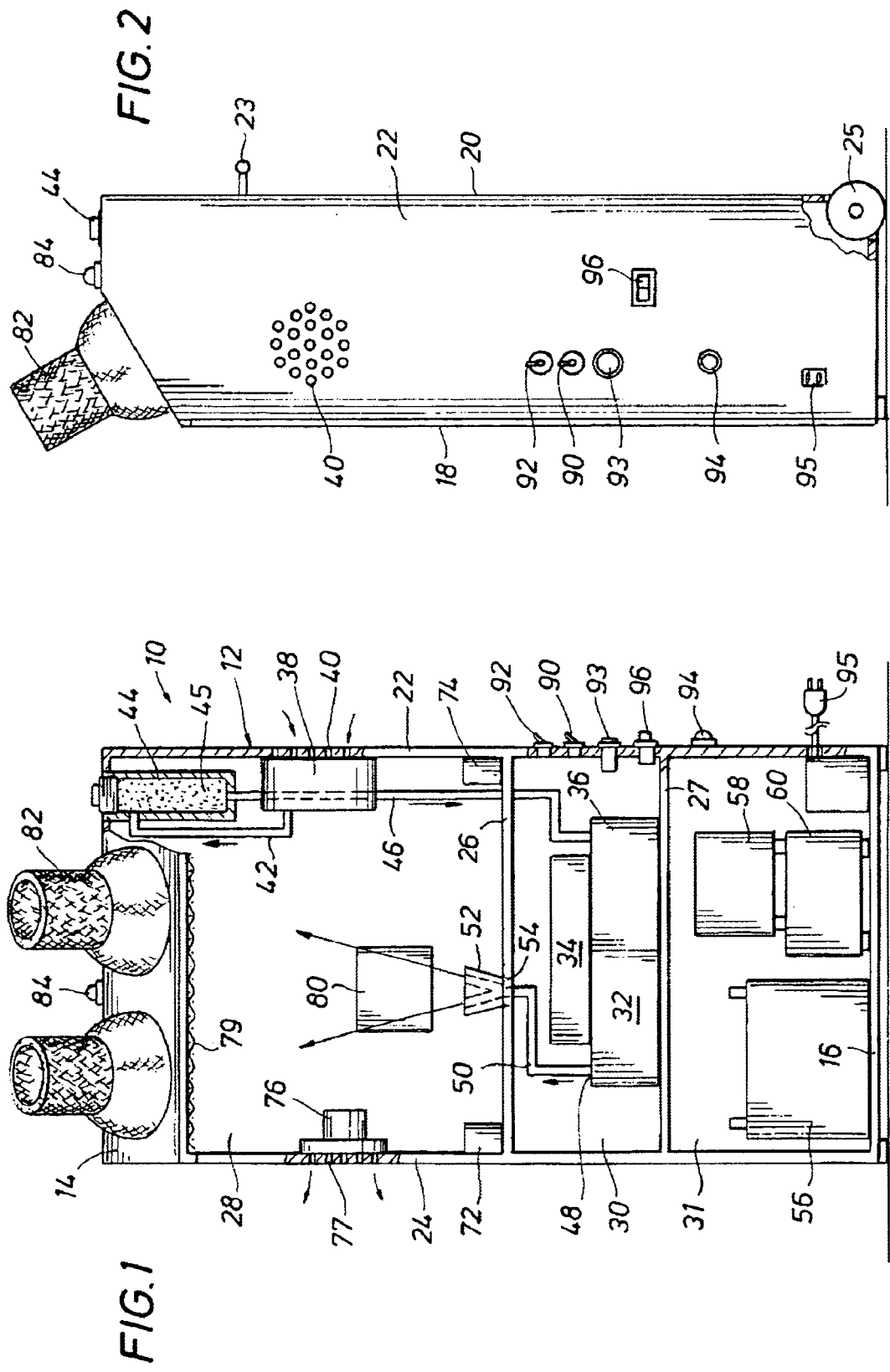

METHOD AND APPARATUS FOR USING OZONE AS DISINFECTANT

BACKGROUND OF THE DISCLOSURE

The present invention relates to apparatus and methods for using ozone as a disinfectant. More specifically, this invention relates to apparatus and methods for killing harmful bacteria that may be transmitted from health care providers to patients.

The Centers for Disease Control and Prevention estimate that 2.4 million hospitalized patients contract an infection every year and that half could be prevented by proper hand washing by health care providers. These infections cause or contribute to 100,000 deaths each year. While medical professionals and staff members follow infection control procedures, it is time consuming to completely clean all skin surfaces when washing hands between patients or before performing a surgical procedure. Most hand cleaners for killing harmful bacteria that can be transmitted to patients are detergent-based products and require several minutes to throughly wash the hands and arms.

Thus, a need remains for a disinfectant which may be used to quickly and conveniently kill harmful bacteria. Ozone is a well known oxidant that destroys bacteria, viruses and other microorganisms on contact. Ozone, or O3, is an allotropic form of oxygen produced from air or other gasses containing oxygen by passage of a stream of such gasses through a high voltage electrical discharge. Contaminants, such as bacteria, which come in contact with ozone are ruptured in a process known as cell lysing. Destruction of the contaminant is almost immediate. This and other benefits of ozone are well known. However, unlike many other disinfecting agents, ozone is used as it is generated, breaks down rapidly and does not leave chemical residues.

It is therefore an object of the present invention to provide a portable ozone generator for use in a medical environment, such as a doctor's office or hospital, for use by health care providers to disinfect their hands and arms between patients.

It is another object of the present invention to provide an ozone generator that is self contained and automatically actuated for bathing the hands and forearms (up to the elbow) of a user in ozone for a predetermined period of time sufficient for completely destroying bacteria, viruses or other microorganisms.

It is another object of the present invention to provide an ozone generator which exhausts ozone through an ozone neutralizing fabric for maintaining ozone concentrations in ambient air in the area around the ozone generator within tolerable limits.

It is a further object of the present invention to provide an ozone generator which may be manually set for repeated and substantially continuous use.

It is another object of the present invention to provide a method which utilizes ozone to destroy bacteria, viruses and other harmful microorganisms.

SUMMARY OF THE INVENTION

In accordance with the present invention, an apparatus for generating an effective concentration of ozone for killing bacteria, viruses and other harmful microorganisms is provided. The apparatus includes a housing having an upper chamber defining an enclosed space for containing elevated concentrations of ozone. The ozone chamber includes ports providing access to the interior of the ozone chamber. The lower chamber of the apparatus houses an ozone reactor and logic circuitry which is programmable and operates both the ozone reactor and a pump for pumping ambient air through a moisture removing filter and then to the ozone reactor. Preferably, the logic circuitry comprises either a microprocessor and data entry switches or a keypad, or an on/off cycling timer relay and a programmable time delay relay. The logic circuit includes a motion detector mounted in the upper chamber for activating the ozone generator of the invention and initiating the generation of ozone directed into the upper ozone chamber of the apparatus of the invention.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 1 is a perspective, partially broken away view of the ozone generating apparatus of the invention;

FIG. 2 is a side view of the ozone generating apparatus of the invention; and

DETAILED DESCRIPTION OF A PREFERRED EMBODIMENT

Figure 3:
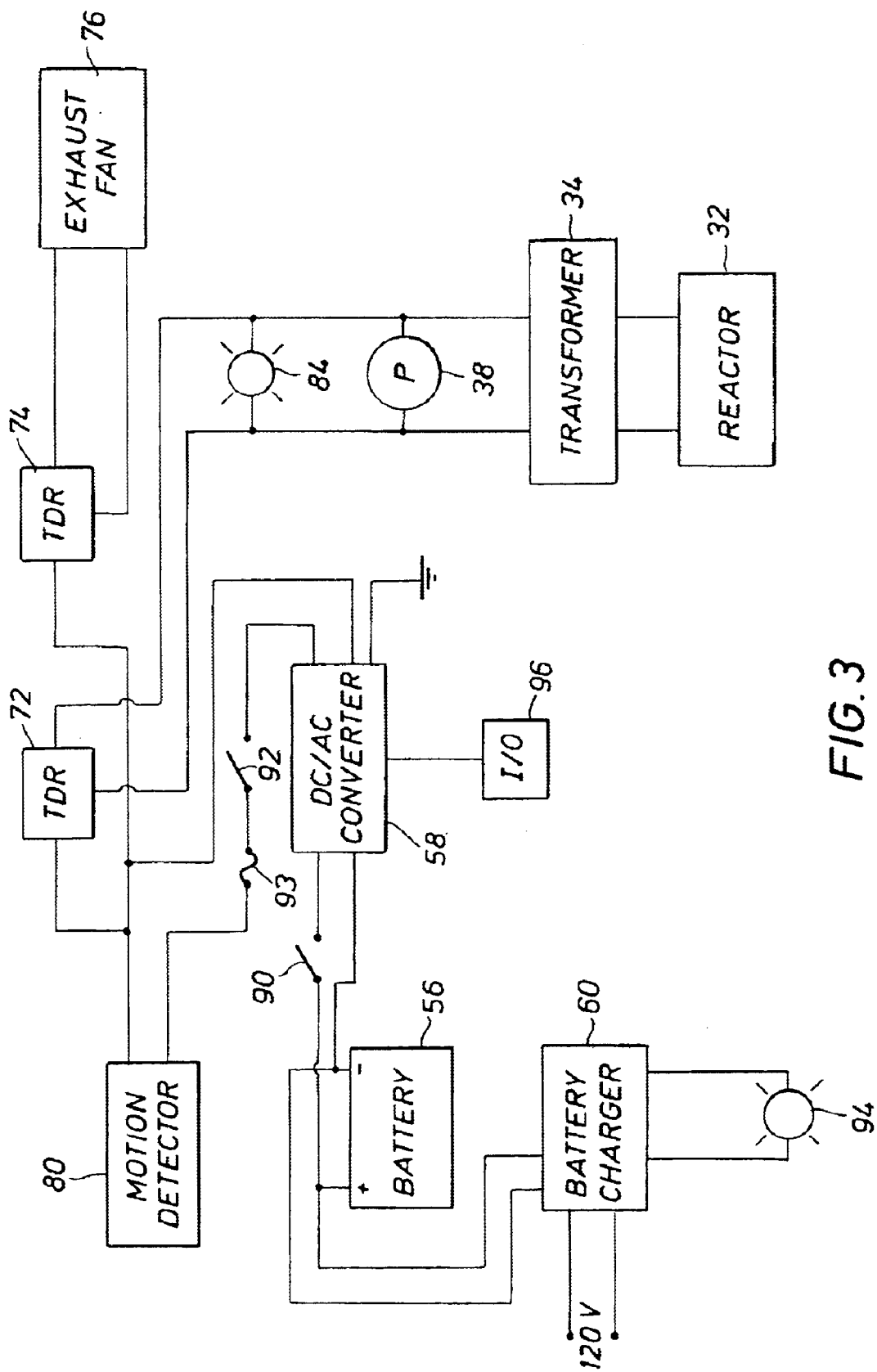
FIG. 3 is a simplified electrical diagram of the ozone generating apparatus of the invention.

Referring first to FIG. 1, the ozone generating apparatus of the invention is generally identified by the reference numeral 10. The ozone generator 10 comprises a housing 12 having top and bottom panels 14 and 16, front and rear panels 18 and 20, and side panels 22 and 24. The housing 12 is formed of materials resistant to ozone oxidation, such as stainless steel sheet metal, PVC or other plastic materials. The housing 12 includes a handle 23 and rollers 25 mounted thereon for conveniently transporting the ozone generator 10. A shelf 26 divides the housing unit 12 into two compartments of approximately equal size. The upper compartment 28 defines an enclosed space for the ozone generated by the apparatus of the invention. The lower compartment is further divided by a shelf 27 to form a reactor compartment 30 and a battery compartment 31. The shelves 26 and 27 in a preferred embodiment may be PVC sheets adhesively secured or otherwise mounted within the housing 12.

The lower compartment of the housing unit 12 houses the operating components of the ozone generator 10 which include an ozone reactor 32 and a transformer 34 located within the reactor compartment 30. The reactor 32 includes an inlet 36 for receiving air directed to the reactor 32 by a pump 38. The pump 38 may be a simple linear pump having air inlets 40 open to ambient air. The pump 38 draws ambient air through the pump inlet holes 40 and directs the air through a line 42 to a dryer 44 for removing water vapor from the ambient air. The dryer 44 passes the air through a silica gel filter 45 which removes water vapor from the air. The dry air is pumped through a line 46 to the inlet end 36 of the reactor 32.

The transformer 34 converts input line voltage to higher voltage for supplying high voltage to the ozone reactor 32 for generating ozone. The transformer 34 preferably is a step-up, high voltage transformer that can receive standard household line voltage so that an operator can safely and conveniently plug the unit into a suitable wall outlet. The transformer 34 creates a high voltage across the reactor 32 so that as air passes through the reactor 32, ozone is created and flows out the outlet 48 of the reactor 32.

The ozone generated by the reactor 32 flows through a line 50 terminating at a nozzle 52. The nozzle 52 is mounted on the shelf 26 and projects into the compartment 28. A silicone rubber collar 54 secures the nozzle 52 to the shelf 26. Ozone generated by the reactor 32 is pumped into the compartment 28 through the nozzle 52.

Referring still to FIG. 1, the ozone generator 10 is preferably equipped with a battery 56 to operate the generator 10 in the event AC power is not available. The battery 56 is connected to a DC to AC converter 58 for supplying AC voltage to the transformer 34. For convenience, the battery 56, converter 58 and a battery charger 60 are housed within the battery compartment 31. The battery compartment 31 is enclosed by a removable cover panel (not shown in the drawings) secured across the lower end of the housing unit 12.

Referring now to FIG. 3, the ozone generator 10 of the invention includes an electrical control circuit for operating the electrically connected components of the invention. The control circuit includes an interval on timer 72 and a time delay relay 74. The interval on timer 72 is set for a predetermined run time where ozone is generated and routed into the upper compartment 28 of the housing unit 12. Activation of the interval on timer 72 is initiated and referenced from the time of application of AC voltage to the transformer 34. The time delay relay 74 is operatively connected to an exhaust fan 76 for removing both ozone and air from the upper compartment 28. The control circuit is activated by a motion detector 80 mounted in the upper compartment 28.

The control circuit is pre-set to operate the ozone generator 10 for a predetermined run cycle. At the end of the control circuit run cycle, the motion detector resets for the next use of the ozone generator 10. By way of example, in the preferred embodiment described herein the control circuit run time is arbitrarily set at 60 seconds. The run time for the interval on timer 72 is set at 30 seconds. During the run time of the interval on timer 72, ozone is generated by the ozone reactor 32 and routed into the ozone compartment 28. Activation of the time delay relay 74 is delayed for 25 seconds after activation of the interval on timer 72, at which point the time delay relay 74 energizes the exhaust fan 76 for 35 seconds for drawing both ozone and air from the ozone compartment 28 into the ambient air surrounding the ozone generator 10. The run cycle for the control circuit of the ozone generator 10 may be set for a shorter or longer time interval as desired to insure the destruction of all contaminants on the health care providers' hands and forearms.

Referring again to FIG. 1, the upper compartment 28, in a preferred embodiment of the invention, is an enclosed space adapted for receiving the hands and forearms of a health care provider or other user therein. The upper compartment 28 is sized to comfortably receive the hands and forearms of the health care provider or other user of the ozone generator 10, but is sufficiently small so that the ozone concentration in the upper compartment 28 quickly achieves a disinfectant level or concentration upon activation of the control circuit. Arm holes formed in the top panel 14 of the housing unit 12 provide access to the upper compartment 28. Elastic sleeves 82 circumscribe the arm holes and provide a passage for insertion of hands and forearms into the ozone compartment 28. The top panel 14 includes a portion which slopes downwardly to the front of the housing 12 so that the arm holes are more conveniently oriented for inserting the hands and forearms into the upper compartment 28. The sleeves 82 provide a seal about the forearms of the health care provider sufficient to prevent ozone from escaping through the arm holes into the surrounding ambient air when the ozone generator 10 is in use. A visual indicator 84 lights up when the control circuit is energized to indicate that ozone is being generated. At the end of the ozone generating run cycle, the light indicator 84 turns off to signal the user of the completion of the disinfectant cycle.

As noted above, the control circuit includes a time delay relay 74 electrically connected to an exhaust fan 76 for removing ozone and air from the upper compartment 28. The fan 76 blows ozone and air through one or more outlet holes 77 formed through a wall of the housing 12. The exhaust outlet holes are covered by a fabric, such as wool, which reacts with the ozone so that the air expelled through the outlet holes 77 into the environment surrounding the ozone generator 10 is substantially free of ozone. Neutralization of ozone is further aided by wool fabric 79 mounted on one or more of the interior walls of the compartment 28, as for example to the bottom of the top panel 14 of the housing 12.

Various and sundry switches and indicators are provided as necessary for the proper operation of the ozone generator 10. For example, an on/off power switch 90 may be turned to the OFF position during maintenance activities to insure that the ozone generator 10 is not inadvertently activated while the unit is undergoing routine maintenance. A switch 92 may be manipulated to convert the ozone generator 10 to DC operation. A charge light 94 provides a visual indication when the battery 56 is being charged and when charging is complete. A fuse 93 is incorporated in the control circuit as an added safety measure. The battery charger 60 includes a power cord 95 for connecting it to an available electrical outlet. In the event immediate repeated use of the ozone generator 10 is required, an I/O power switch 96 may be set to the OFF position and back to the ON position to bypass the delay time required for the motion detector 80 to reset. The ozone generator may thus be set for substantially continuous use as circumstances may require.

The ozone generator described above and as represented in the drawings is adapted for both AC and DC operation. In the DC mode, power switches 90 and 92 and the I/O power switch 96 are set to the ON position. Insertion of a health care providers hands and forearms through the arm holes 82 energizes the motion detector 80 which applies electrical voltage to the control circuit. The indicator light 84 illuminates to indicate that the system is energized and ozone is being generated by the reactor 32. The interval on timer 72 and time delay relay 74 are energized and operate for a preset run cycle. The pump 38 pulls in ambient air through the drier 44 and into the reactor 32. Moisture in the air is removed as it passes through the silica gel filter 45 housed in the drier 44. The air is converted into ozone as it passes through the reactor 32 and is routed into the upper compartment 28 for contact with the hands and forearms of the health care provider to kill any bacteria, viruses or microorganism thereon. The interval on timer 72 is preset for a thirty second run cycle which is sufficient to generate an ozone concentration level in the upper compartment 28 to properly disinfect the health care providers hands and forearms.

In the preferred embodiment of the invention described above, disinfecting the hands and forearms of health care providers has been described for illustrative purposes. It is understood that the ozone generator of the invention may be configured for disinfecting other parts of the body as may be required. For example, the ozone compartment 28 may be configured to accept the upper torso of a patient, or the legs or the entire upper and lower torsos to be bathed in ozone for destroying bacteria, viruses and other microorganisms. The ozone compartment 28 may also be configured to function as an autoclave for sterilizing dental and surgical instruments.

While a preferred embodiment of the invention has been shown and described, other and further embodiments of the invention may be devised without departing from the basic scope thereof, and the scope thereof is determined by the claims which follow.

What is claimed is:

1. An ozone generator comprising:
   a) a housing contoining first and second enclosed compartments;
   b) said first compartment including access means permitting a user's hands and forearms to be inserted into said first compartment;
   c) ozone generating means housed in said second compartment of said housing;
   d) a conduit having one end connected to an outlet end of said ozone generating means and an opposite end opening into said first compartment;
   e) means for controlling the operation of said ozone generating means; and
   f) means for automatically activating said ozone generating means upon insertion of a user's hands and forearms into said first compartment.

2. The apparatus of claim 1 including a pump for pumping ambient air to said ozone generating means.

3. The apparatus of claim 2 including a silica gel filter for removing water vapor from the air pumped into said ozone generating means.

4. The apparatus of claim 1 including a control circuit for controlling operation of said ozone generating means.

5. The apparatus of claim 4 wherein said control circuit includes a timer for controlling the run cycle of said ozone generating means.

6. The apparatus of claim 5 including a time delay relay circuit operatively connected to an exhaust fan and set for delayed operation for removing ozone from said first enclosed compartment.

7. The apparatus of claim 1 wherein said activating means includes a motion detector housed in said first enclosed compartment for energizing a control circuit for activating said ozone generating means upon sensing motion in said first enclosed compartment.

8. The apparatus of claim 7 including a bypass switch for bypassing said motion detector for repetitive and continuos operation of said ozone generator.

9. The apparatus of claim 1 including a DC to AC converting circuit for operation of said ozone generating means.

10. The apparatus of claim 1 wherein said first enclosed compartment includes fabric mounted on one or more interior walls thereof for neutralizing ozone generated by said ozone generating means.

11. The apparatus of claim 1 wherein said access means comprises arm holes formed in a top panel of said first compartment.

12. The apparatus of claim 11 including sleeves circumscribing said arm holes providing a passageway for inserting a user's arms and forearms into said first compartment.

13. An ozone generator comprising:
   a) a housing containing first and second enclosed compartments;
   b) said first compartment including access means permitting a user's hands and forearms to be inserted into said first compartment;
   c) ozone generating means housed in said second compartment of said housing operatively connected to a control circuit for activating said ozone generating means, and wherein upon activation said ozone generating means releases ozone into said first compartment; and
   d) wherein said first compartment includes fabric mounted on the interior thereof for aiding in the neutralization of ozone within said first compartment.

* * * * *